United States Patent

Freeman

[11] Patent Number: 5,681,579
[45] Date of Patent: Oct. 28, 1997

[54] POLYMERIC SUPPORT WOUND DRESSING

[75] Inventor: Frank Freeman, Abaco, Bahamas

[73] Assignee: E.R. Squibb & Sons, Inc., Princeton, N.J.

[21] Appl. No.: 197,047

[22] Filed: Feb. 23, 1994

Related U.S. Application Data

[63] Continuation-in-part of Ser. No. 35,352, Mar. 22, 1993, abandoned.

[51] Int. Cl.[6] .......................... A61L 15/28; A61L 15/32; A61L 15/60
[52] U.S. Cl. .......................... 424/448; 424/447; 602/44; 602/47; 602/49; 602/50; 602/54
[58] Field of Search .......................... 424/449, 443, 424/445, 447, 448; 602/44, 47, 49, 50, 54, 55, 56, 52; 428/246, 247, 308.4, 481, 509

[56] References Cited

U.S. PATENT DOCUMENTS

| | | | |
|---|---|---|---|
| 4,341,207 | 7/1982 | Steer et al. | 128/155 |
| 4,538,603 | 9/1985 | Pawelchak et al. | 128/156 |
| 4,551,490 | 11/1985 | Doyle et al. | 524/22 |
| 4,738,257 | 4/1988 | Meyer et al. | 128/56 |
| 4,773,409 | 9/1988 | Cliento et al. | 128/156 |
| 4,793,337 | 12/1988 | Freeman et al. | 128/156 |
| 4,837,025 | 6/1989 | Guillemet et al. | 424/448 |
| 4,972,829 | 11/1990 | Knerr | 128/155 |
| 4,977,892 | 12/1990 | Ewall | 128/156 |
| 4,995,382 | 2/1991 | Lang et al. | 128/156 |
| 4,997,656 | 3/1991 | Shikinami et al. | 424/448 |
| 5,060,662 | 10/1991 | Farnsworth, III | 128/888 |
| 5,092,323 | 3/1992 | Riedel et al. | 602/54 |
| 5,244,457 | 9/1993 | Karami et al. | 602/55 |

FOREIGN PATENT DOCUMENTS

| | | |
|---|---|---|
| 0190814 | 1/1986 | European Pat. Off. |
| 0292080 | 5/1988 | European Pat. Off. |
| 0509703 | 7/1992 | European Pat. Off. |
| 9205755 | 4/1992 | WIPO |
| 9300056 | 1/1993 | WIPO |

*Primary Examiner*—Edward J. Webman
*Attorney, Agent, or Firm*—John M. Kilcoyne; Theodore R. Furman, Jr.

[57] ABSTRACT

In accordance with the present invention a novel wound dressing providing superior absorption and preventing leakage is disclosed. The present dressing comprises a hydrocolloid-containing polymeric support layer either continuous or non-continuous and an occlusive backing layer overlying the support. In a preferred embodiment the present dressing further includes an adhesive on a skin-contacting surface of the support and an absorbent region interposed between the support and the backing layer.

26 Claims, 4 Drawing Sheets

POLYMERIC SUPPORT WOUND DRESSING

This application is a continuation in part of U.S. application Ser. No. 035,352 filed on Mar. 22, 1993, now abandoned.

BACKGROUND OF THE INVENTION

The present invention is directed to new wound dressings that have a superior ability to absorb wound fluid and prevent dressing leakage and wound maceration. The dressings of the present invention are particularly adapted for application on wounds that heavily exudate wound fluids during the healing process. There are numerous dressing products in the art that are used in treating patient wounds in medical applications, however, these products do not achieve the beneficial results of the present invention for these heavily exudating wounds.

Chen in U.S. Pat. No. 3,339,546 discloses an adhesive composition comprising a blend of one or more water soluble or water swellable hydrocolloids and a viscous substance such as polyisobutylene. The adhesive mass has a film of water insoluble material affixed to one surface. Such a bandage is commercially available under the trademark Stomahesive from Bristol Myers Squibb Company and is employed primarily as a skin barrier by ostomates.

Pawelchak et al. in U.S. Pat. No. 4,393,080 discloses adhesive compositions for medical use comprising an homogeneous mixture of polyisobutylenes and one or more natural or synthetic polymers, capable of developing elastomeric properties when hydrated, such as gluten and long chain polymers of methyl vinyl ether/maleic acid. The composition may also include one or more water soluble hydrocolloid gums and may additionally contain one or more water swellable cohesive strengthening agents. Additionally, one or more thermoplastic elastomers such as styrene copolymers and small mounts of mineral oil may be included within the composition.

Pawelchak et al. in U.S. Pat. No. 4,538,603 discloses an occlusive dressing comprising a first adhesive layer which contacts the skin and wound, a semi-open cell elastic foam layer, and a film overlying said foam layer. A second more aggressive adhesive layer is interposed between said first adhesive and foam to more suitably accommodate the difference in the adhesive requirements for the skin and the foam. This structure, based on a fluid-interactive adhesive, provides an excellent wound dressing which has enjoyed much commercial success in that the integrity of the structure is enhanced by the presence of the second adhesive.

The fluid-interactive adhesive of Pawelchak is one in which a considerable portion of the fluids must be able to permeate through, or be absorbed into, the adhesive while the adhesive still maintains enough "wet tack" to adhere to the wound and the surrounding normal skin. As the adhesive interacts with large amounts of fluids (such as over extended periods of time and/or due to heavy fluid flow), it typically becomes gel-like. Even though the designed-in "wet tack" properties maintain contact between the wound and the adhesive, the tenacity of the bond at the wound dressing/adhesive interface can be adversely affected.

Thus, since such fluid-interactive materials of the Pawelchak-type adhere to the wound for extended periods, in many cases it is ultimately the loss of adhesion to the product, wound dressing, tape or film that necessitates replacement thereof. For example, the wound fluids may eventually permeate the first adhesive and are believed to have a deleterious effect on the second adhesive. Often it is the resulting separation of the semi-open cell foam and polyurethane film from the adhesives, and not slippage of the adhesive, from the skin or wound, that makes a dressing change necessary. This is especially true for wounds emitting large amounts of fluids.

Doyle et al. in U.S. Pat. No. 4,551,490 discloses pressure sensitive adhesive compositions for medical uses with particular application in the fields of incontinence, ostomy care and wound and burn dressings. The adhesive compositions are generally a homogenous blend of mineral oil, one or more polyisobutylenes or mixtures of one or more polyisobutylenes, and an elastomer such as butyl rubber, styrene random or block-type copolymers, water soluble hydrocolloid gums, water swellable cohesive strengthening agents and small amounts of various other optional ingredients.

In Freeman et at., U.S. Pat. No. 4,793,337, there is disclosed an adhesive structure for adhesion of an article to a fluid emitting wound and the surrounding skin. The adhesive structure comprises a first contact region comprised of a fluid-interactive adhesive material which provides adhesion to the wound and surrounding normal skin and a second contact region comprised of the same or different adhesive material which provides adhesion between the first region or another region integral with the first region and the article. An absorbent region comprised of an absorbent fiber, fabric, or foam material is present intermediate the first and second regions whereby enhanced cohesion between the first and second regions and between the second region and the article is provided.

Cheong in European Patent Application 92300815.5 discloses a net dressing in which the net substrate is encapsulated in a hydrophilic, tacky resin. The substrate used in a net dressing is an apertured material where the apertures generally have a diameter or width of 0.5 to 5 mm. The substrate is encapsulated so that the majority of the apertures in the net substrate are non-occluded.

It has been found that there are numerous problems in the present dressings in that they generally do not have the ability to sufficiently absorb wound fluid or to do so at the rate at which it is produced by the body. This leads to dressing leakage and wound maceration. These problems are particularly present in dressings based on polymers such as polyisobutylene (PIB) and/or styrene copolymers such as styrene-butadiene-styrene (S-B-S), styrene-isoprene-styrene (S-I-S) and styrene-ethylene/butylene-styrene (S-EB-S) of which Kraton is a commercial example. Another problem present in dressings which are PIB-based dressings is that the PIB is frequently eroded by water or other fluids present in the wound. One commercial dressing is a dressing sold under the trademark Duoderm. While this dressing is an excellent all-around dressing, it does not provide a dressing that can absorb the wound fluids of heavily exudating wounds as is described in some applications. Difficulties may be encountered with this dressing because it may not absorb wound fluid at the rate it is produced by the body.

The art has attempted to solve the problem of dressings for the absorption of wound fluid from heavily exudating wounds by using Kraton-type materials. Although Kraton is superior for wound dressings in many instances it is unable to provide a suitable dressing where there are heavily exudating wounds. The present invention provides a wound or ostomy dressing which avoids these problems and provides superior wound absorption, particularly for wounds that are heavily exudating wound fluid.

OBJECTS OF THE INVENTION

It is an object of the present invention to provide a new hydrocolloid dressing that has superior absorption ability.

It is an object of the present invention to provide a new hydrocolloid dressing that is able to absorb wound fluid at a greater rate for longer periods of time.

It is also an object of the present invention to provide a new hydrocolloid dressing that reduces the risk of leakage of wound fluid.

It is a further object of the present invention to provide a new hydrocolloidal dressing that reduces the risk of wound maceration.

It is another object of the present invention to provide a wound dressing that has a clean appearance for a longer period of time, thus reducing the need for premature replacement of the dressing by the care giver.

SUMMARY OF THE INVENTION

In accordance with the present invention a novel wound dressing providing superior absorption and preventing leakage is disclosed. The present dressing comprises a hydrocolloid-containing polymeric support layer either continuous or non-continuous and an occlusive backing layer overlying the support. In a preferred embodiment the present dressing further includes an adhesive on a skin-contacting surface of the support and an absorbent region interposed between the support and the backing layer.

DETAILED DESCRIPTION OF THE INVENTION

The present invention provides a unique approach to wound care in that the novel dressing disclosed herein can provide for the rapid uptake of wound exudate away from the wound, while still providing a moist, occlusive, hydrocolloid environment for wound healing. Whereas prior art dressing contain hydrocolloids within an adhesive gel or mass, the present invention incorporates hydrocolloids into a noncontinuous polymeric support. By "noncontinuous" is meant that the polymeric support is either a web, net, perforated layer or perforated film of the polymeric material. Thus, the noncontinuous nature of this polymeric support provides pathways for the rapid uptake of wound or body fluids while at the same time providing for beneficial interaction of the hydrocolloids with the wound itself. The noncontinuous net, web, perforated film or perforated layer is generally much thinner than the hydrocolloid-containing adhesive gel counterparts since such webs or nets, etc., are on the order of 0.5 mils to 2 or 3 mils in thickness. Dressings of this invention, especially those embodiments incorporating an adhesive and an absorbent region, are useful in other medical applications, e.g., as ostomy baseplates.

Figure 1:
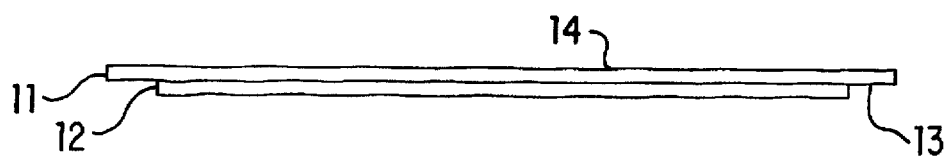
FIG. 1 is a side view of an island dressing of the present invention where the dressing is comprised of two layers, an occlusive layer and a hydrocolloid containing polymeric layer.

As shown in FIG. 1, the hydrocolloid dressing of the present invention is provided with an occlusive film layer 11. The occlusive layer 11 has an upper or outer surface 14 which is open to the atmosphere and an inner surface 13 which is the side toward the skin. This layer is selected from a material that is generally impervious to fluid transmission. The occlusive layer preferably has a moisture vapor transmission rate (MVTR) in the range of about 100 to 800, although the upper limit for some applications can be as high as 4000 or greater, as may be required. The latter MVTR would be preferred in instances where larger dressings are needed and treatment requires that a portion of the wound fluid be evaporated through the dressing. The occlusive layer 11 may be made of any soft film having a MVTR within the above range. Some preferred materials include polyurethanes, polyolefins such as linear low density polyethylene, low density polyethylene and ethylene vinyl acetate, Sarans materials such as vinylidene chloride copolymers of vinyl chloride, methyl acrylate, or methyl methacrylate copolymers. A preferred polymeric material is polyurethane, either as a film or as a polyurethane foam. The polyurethane could be an ester or ether based polyurethane having a 6800 psi and an elongation of from 300 to 750. The water vapor transmission rate (WVTR) of such polyurethane is preferably from 100–4000 (ASTM). One preferred polyurethane film is Medifilm. Other materials which can be used in the occlusive layer are styrene copolymers such as styrene-butadiene-styrene (S-B-S), styrene-isoprene-styrene (S-I-S) and styrene-ethylene/butylene-styrene (S-EB-S), methyl methacrylate, copolymers and nitrile rubber.

Another material that may be used as the occlusive layer is a foam or fiber combination where there is a layer of foam or fiber which has a film layer adhered thereto. The foam used in these dressings is generally a polyethylene or polyurethane foam laminated to about 0.5 mil polyester film. The foam preferably has a density of about 0.042–0.057 gm/sq. in. The fiber material may be any suitable non-woven fabric, either with or without a superabsorbent being present. The fiber preferably has a wicking capability to aid in wound fluid removal. The superabsorbent may be a superabsorbent such as Salasorb 84/90 or equivalent and may be given a delayed absorption characteristic by coating the superabsorbent material with ethyl cellulose, cellulose acetate hydrogen phthalate, cellulose acetate phthalate, Eudragit resin, hydrocolloids such as gelatin/pectin/guar gum or pharmaceutical grade of shellac, or other materials used in pharmaceutical delayed release preparations.

In the embodiment of FIG. 1, the dressing of the present invention has a polymeric support layer 12 adhered to the occlusive layer by a suitable means. One such bonding means is the use of adhesive provided on the surface of the occlusive layer 13. This adhesive may for example extend across the entire under surface 13 of the occlusive layer or only a portion of it. An alternate bonding means is, for example, heat or ultrasonic bonding. As seen in FIG. 1, the dressing is in an island form where there is adhesive material that is not covered by polymeric support layer 12 and which can be used to adhere the dressing to the patient. The polymeric support layer 12 can be of any polymeric material useful in medical settings and is in the form of a web, net, perforated film or perforated layer. Suitable materials include polyolefins such as polyethylenes (with and without acetate moieties, e.g., ethylene vinyl acetate), polypropylenes, polyesters and the like. Other suitable polymeric materials include water soluble polymers such as polyvinylpyrrolidones, polyvinyl-alcohols and the like. One such preferred polymeric material is ethylene vinyl acetate (EVA), available for example as Union Carbide's Natural 7 or EVATANE 1020 VN5 or 1080 VN5. The EVA preferably has a VA content of about 15 to 28% and more preferably about 18%. The polymeric material, such as EVA, preferably has a melting temperature of about 105° C. or below since at temperatures above 105° some degradation of hydrocolloids is possible. Polymeric support layer 12 contains a hydrocolloid either blended with the polymeric material or coated thereon. When the hydrocolloid is blended with the polymeric material it is preferred that the two materials be extruded together to form a film. The layer 12, when it is a blend of hydrocolloid and a polymeric material, can be formed by any suitable process. One process that has been found to be suitable is the use of a twin screw extruder to extrude the polymeric material such as granulated EVA. The extradate is then re-extruded and the hydrocolloid material is mixed into the EVA in a section of the screw. The EVA containing hydrocolloidal material is then extruded to form a film which can be laminated or adhered to the occlusive layer by any conventional process.

Prior to adhering the so formed hydrocolloidal containing layer to the occlusive layer it is perforated to provide a fluid path for the wound fluids. The perforations may be formed by any suitable means. One such means of perforating the film is by passing the film over a heated roll or, alternatively the holes are punched into the film mechanically. Another method of perforating the film is by extruding the film, embossing it on a roll and biaxially orienting the film. It is preferred that there be at least 40 perforations to a square inch.

In an alternate embodiment of the invention, the polymeric support layer 12 can be a thin perforated polyethylene or polypropylene film such as that sold under the trademark Delnet. This thin perforated film can be coated with the hydrocolloid material by suitable means. In one method of applying the hydrocolloidal material, the hydrocolloid can be applied by coating a thin perforated film with a 2 or 3% solution of the hydrocolloid in water. When an aqueous solution of hydrocolloid is being applied to the thin perforated film, the thin film may be corona treated to promote adhesion of the hydrocolloid. In an alternative embodiment, a solution such as a 10% suspension of hydrocolloid in a gelled mineral oil, petroleum jelly, a suppository base such as HulsWitespol Softisan, or other suitable carrier may be used. The suppository base is generally a vegetable fatty acid having a C10–C18 length carbon chain.

The hydrocolloid materials useful in the present invention include any water soluble gum (e.g. pectin, guar gum, xantham gum), gelatin, carboxymethylcellulose (CMC), such as sodium CMC, sodium or calcium alginates, polysaccharides and the like. The hydrocolloid material may also include additional materials such as antibiotics or growth factors and silver sulfadiazine or other antibacterial products. The hydrocolloid may be present in the polymeric support layer 12 either with or without accelerators to promote release, such as surfactants, known in the art.

Figure 2:
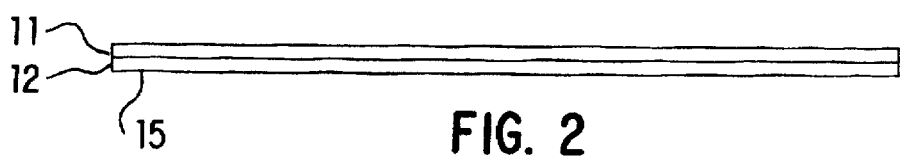
FIG. 2 is a side view of an alternate embodiment of the dressing of FIG. 1.

FIG. 2 shows an alternate embodiment where there is the occlusive layer 11 and the polymeric support layer 12. The adhesive for adhering the dressing to the patient is placed on surface 15 of polymeric support layer 12. The adhesive may be across the entire surface of layer 12 or may be applied only over portion of the surface as desired. For example, the center portion of the surface 15 may be free of adhesive and adhesive is only about the perimeter of the dressing. Also, the adhesive can be noncontinuous, i.e., corresponding to the surface of the noncontinuous polymer support layer 12, or can be a continuous thin film adhesive applied to surface 15. The thickness of this adhesive is preferably about 1–10 mils and more preferably 2–4 mils. The adhesive can be of any of the medical grade adhesives known in the art such as acrylic pressure sensitive adhesives or rubber-based pressure sensitive adhesives. Also the prior art hydrocolloid adhesives are very useful such as those disclosed in U.S. Pat. Nos. 3,339,546 to Chen, U.S. Pat. No. 4,393,080 to Pawelchak et at., U.S. Pat. No. 4,538,603 to Pawelchak et at., the disclosures of which are incorporated herein by reference. Thus, the adhesive may include an homogeneous blend of one or more pressure sensitive adhesive materials and one or more natural or synthetic polymeric materials capable of developing elastomeric properties when hydrated, such as gluten and long chain polymers of methyl vinyl ether/maleic acid. The composition may also include up to 50% by weight of one or more water soluble hydrocolloid gums and may additionally include one or more water swellable cohesive strengthening agents. Additionally, one or more thermoplastic elastomers may be included with the pressure sensitive adhesive materials.

Various natural or synthetic viscous or elastomeric substances such as natural rubber, silicone rubber, acrylonitrile rubber, polyurethane rubber, polyisobutylene, etc., either possessing dry tack by themselves or developing such tack upon the addition of a plasticizer are suitable as adhesives. Low molecular weight polyisobutylenes having a viscosity average molecular weight of from about 36,000 to about 58,000 (Flory) may also be used.

Optionally, one or more thermoplastic elastomers can be included in the pressure sensitive adhesive component. These elastomers impart the properties of rubber-like extensibility and both rapid and complete recovery from modular strains to the pressure sensitive adhesive component. Suitable thermoplastic elastomers include medium molecular weight polyisobutylenes having a viscosity average molecular weight of from about 1,150,000 to 1,600,000 (Florey), butyl rubber which is a copolymer of isobutylene with a minor mount of isoprene having a viscosity average molecular weight of from about 300,000 to about 450,000 (Florey), and styrene copolymers such as styrene-butadiene-styrene (S-B-S), styrene-isoprene-styrene (S-I-S), and styrene-ethylene/butylene-styrene (S-EB-S) which are commercially available, for example, from Shell Chemical Co. under the trademark Kraton as Kraton D1100, Kraton D1102, Kraton D1107, Kraton 4000, Kraton G1600, and Kraton G4600. Thermoplastic elastomers such butyl rubber having a viscosity average molecular weight of about 425,000 (commercially available as gauge 077), polyisobutylene having a viscosity average molecular weight of about 1,200,000 (commercially available under the trademark Vistanex from Exxon as gauge L-100), and styrene-isoprene-styrene (S-I-S) copolymers (commercially available from Shell as Kraton D1107). In the case of polyisobutylene (PIB) based adhesives, a perforated film can be used to support a thin layer of these materials. The perforations permit fluid flow when the PIB disintegrates.

The natural or synthetic polymers which develop elastomeric properties when hydrated may be present at from about 3% to about 60% by weight of the adhesive composition. The preferred materials are the long chain polymers of methyl vinyl ether/maleic acid. The maleic acid moiety in the polymer may be intact (Gantrez S-97), may be an anhydride (Gantrez AN-169), or may be a metal salt such as the mixed sodium/calcium salts (Cantfez AT-955). These materials are hydrophilic and when hydrated, form extensible elastic masses with substantial tack to skin and other surfaces. The adhesive composition may also include up to about 30% by weight of one or more water swellable cohesive strengthening agents, provided that the water soluble hydrocolloid gums and water swellable cohesive strengthening agents together are present at no more than about 60% by weight of said adhesive composition. Suitable water swellable cohesive strengthening agents include finely divided and substantially water insoluble cross-linked sodium carboxymethylcellulose, such as that commercially available under the trademark Aqualon, finely divided and substantially water insoluble starch-acrylonitrile graft copolymer, and finely divided and substantially water insoluble cross-linked dextran.

Figure 3:
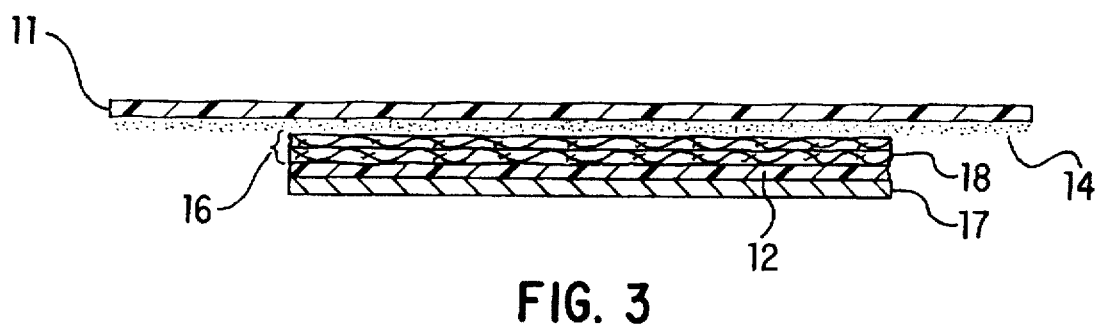
FIGS. 3 and 4 are side views of an alternate embodiments of the present invention where there is an absorbent layer present in the dressing.

Depending on the type of wound and the amount of exudate expected additional layers may also be present in dressing of the present invention. Between the occlusive layer 11 and the polymeric support layer 12 may be an absorbent region 16 as shown in FIG. 3. Additional hydrocolloid material and/or superabsorbents are preferably present in the absorbent region 16 to promote absorption and wound healing.

The material of the absorbent region 16 can be a fabric, foam, fiber or the like, including combinations thereof, which is capable of both absorbing fluids and bonding to the occlusive layer 11 and the polymeric support layer 12. This absorbent region can be made up of the known pulp products either with or without hydrocolloid or superabsorbent material. The absorbency selected depends on the type of wound being treated.

The absorbent region can be any of the materials used in wound care. Materials that may be used in the absorbent region include fabrics, foams or fibers of polyester, polypropylenes, polyethylenes and the which are optionally bonded to polyester film (such as Kendall's Novenette). Other suitable materials include, but are not limited to, natural and synthetic polymeric absorbents, hydrocolloids (as discussed above), superabsorbents, and cellulosic absorbents. Cellulosic materials include cotton, rayon, wood, or cellulose. The superabsorbent material may be in any suitable form. Typical superabsorbents include starch grafted copolymers of acrylate salts, starch grafted copolymers of acrylamide salts, polyacrylate salts and the like, including mixtures thereof. Superabsorbent materials and composites are easily prepared or commercially available. Once such product is the composite air laid superabsorbent pad (dry forming process and the superabsorbent fiber flock SAFF) sold by Hanfspinnern Steen & Company. The superabsorbent may also be a delayed released web superabsorbent.

Superabsorbent webs that may be used in the present invention to serve as, or to be incorporated into, the absorbent region 16 may also include carded or random webs made from, for example, cotton, rayon, polyethylene, polyester, or wool. Another suitable web is a spun-laced web made from polyester, polypropylene, or polyethylene. The superabsorbent webs may also be in the form of tissues either single ply or multiple ply and either creped or uncreped. Delnet, a product of Applied Extrusion Technologies which consists of a range of materials manufactured from polyethylene or polypropylene using extrusion embossing and orientation processes may also be used as a web for preparing a superabsorbent web.

Superabsorbent webs can be formed by any convenient means, e.g., by slightly moistening or misting a web. After misting, a powdered superabsorbent may be applied followed by running the web through a dry oven or heating the roll. The powder adjacent to the moistened web will become tacky and adhere to the adjacent material (fiber, surface), and the loose powder would then be vacuumed off. Alternatively, superabsorbent powder can be sandwiched between nonwoven webs/paper and subjected to moist steam which would make the superabsorbent tacky so that it would then stick to adjacent surfaces. The sandwiched superabsorbent and web would then be dried, creating a two-ply web with superabsorbent between them. The superabsorbent layer can also be heat bonded to the other layers.

As shown in FIG. 3 the absorption region may be a multi-layer laminate 16 having at least two layers. The laminate has a surface layer or wound contact layer 17 preferably made of a non-adhering wound dressing material. The non-adhering wound dressing layer 17 is preferably a fabric manufactured from a polyolefin such as polyethylene or polypropylene. The non-adhering fabric is preferably formed by using an extrusion embossing and orientation process. An example of the non-adhering wound dressing material is Delnet, sold by Applied Extrusion Technologies. An alternative material is a high, wet strength, non-woven, low-lint material impregnated with hydrocolloids carried in a solution of polyvinylpyrolidene (PVP) in isopropyl alcohol. The inner layer 18 of the multi-layer laminate (the layer between the nonadhering wound dressing layer and the absorbent layer) is preferably comprised of a water soluble film such as polyvinylpyrrolidone (PVP), hydroxypropyl cellulose, or hydrocolloid material, and the inner layer between the non-adhering wound dressing layer and the absorbent layer preferably contains the hydrocolloid material. Other layers may be present in the laminate.

Figure 4:
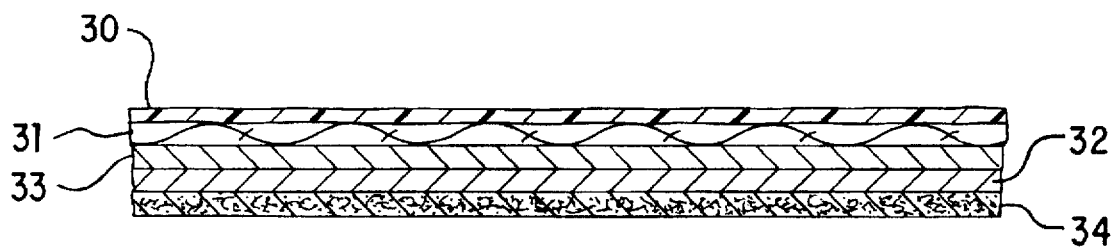
Figure 5:
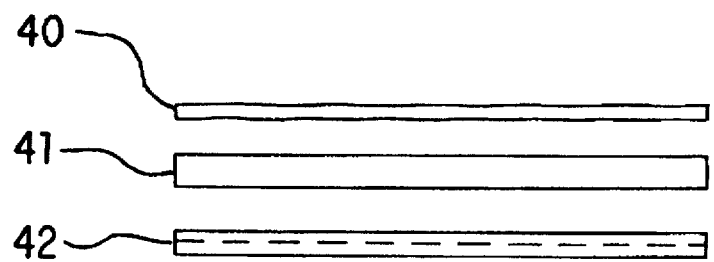
FIG. 5 is a side view of an alternate embodiment of the dressing of the present invention.
Figure 6:
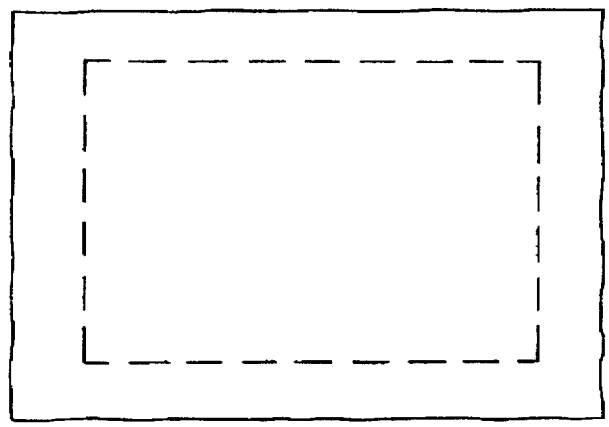
FIG. 6 is a top view of the dressing of FIG. 5.
Figure 7:
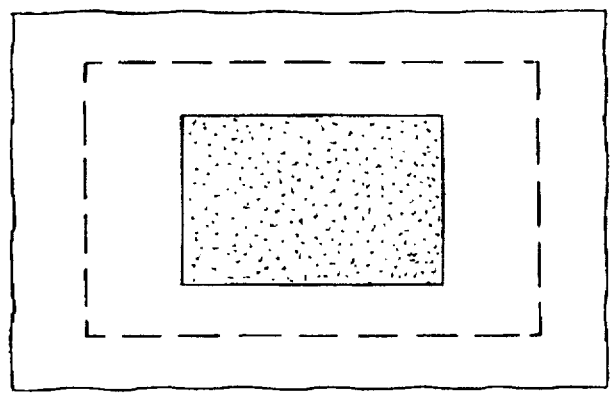
FIG. 7 is a bottom view of the dressing of FIG. 5.

In an alternative embodiment of the present invention shown in FIG. 4, the dressing may have, in order from the outside, an outer or occlusive layer 30, an absorbent layer 31 preferably in contact with the occlusive layer, a non-adhering fabric layer 32, a polymeric support layer 33 of a material having a melting temperature of less than 105° C. and having a coating of a hydrocolloid in a gelled mineral oil petroleum jelly or other coating. Adhesive layer 34 is present on polymeric support layer 33. Additional layers may be also be present. Shown in FIG. 5 is a dressing having an outer or occlusive layer 40 comprised of a polyurethane film or foam or other suitable material. The absorption layer 41 may contain hydrocolloid/polyacrylate absorbents, preferably with a hydrocolloid adhesive applied to the lower surface of the layer. Layer 42 is a polymeric support layer of a material having a melting temperature less than 105° C. The polymeric support layer 42 may be continuous or in a window form as seen in FIG. 6. When in window form, the adhesive layer is only about the perimeter of the dressing and not in its center portion. The location of the adhesive when a window form is used in depicted by the area between the dotted lines and the outer edges of the dressing of FIGS. 6 and 7.

Figure 8:
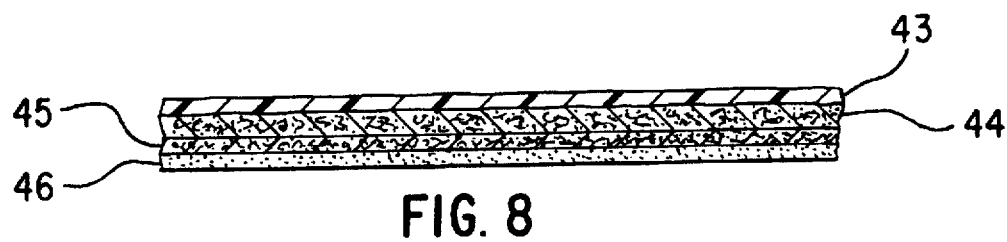
FIG. 8 is a side view of an alternate embodiment of the present invention.

In a further alternative embodiment of the invention, the dressing, FIG. 8, may have in order from the outside: an outer or occlusive layer 43, an absorbent layer of polyolefin fibers 44 containing a hydrocolloid either alone or coated with delayed absorption materials, and a polymeric film 45 of a material having a melting temperature less than 105° C. This layer has a film layer 45 coated with a hydrocolloid and adhesive layer 46.

Figure 9:
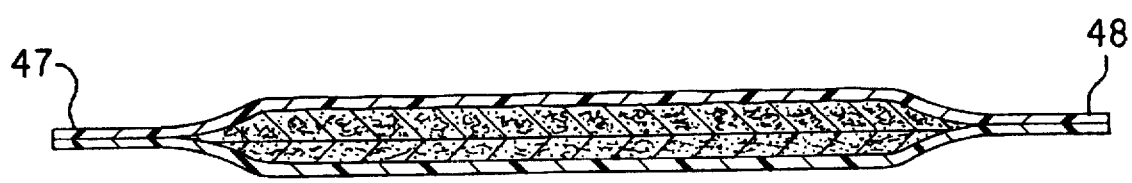
FIG. 9 is the dressing of FIG. 8 wherein the edges are heat sealed on the perimeter.
Figure 10:
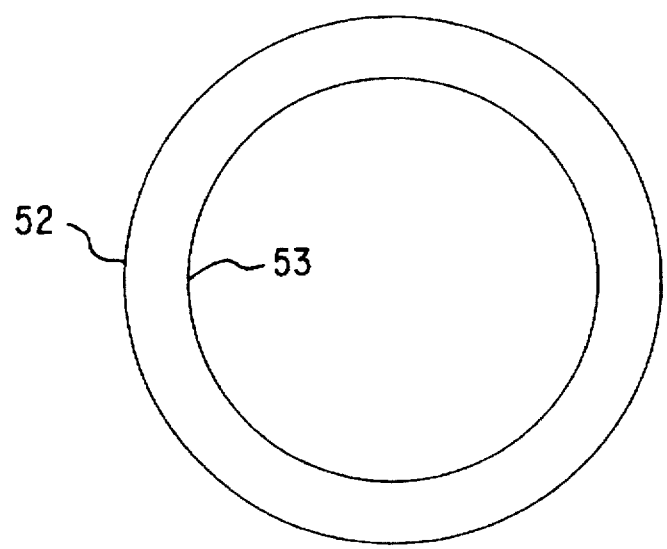
FIG. 10 is a top view of the dressing of FIG. 8 wherein the edges are heat sealed in an area adjacent its edges.
Figure 11:
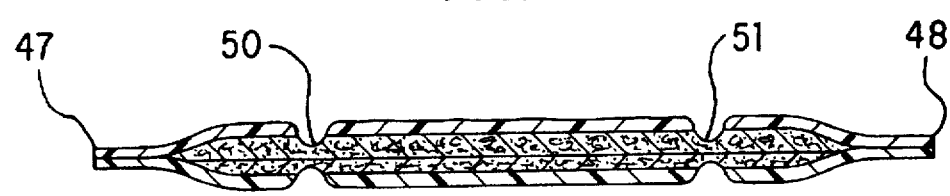
FIG. 11 is a side view of the dressing of FIG. 10.
Figure 12:
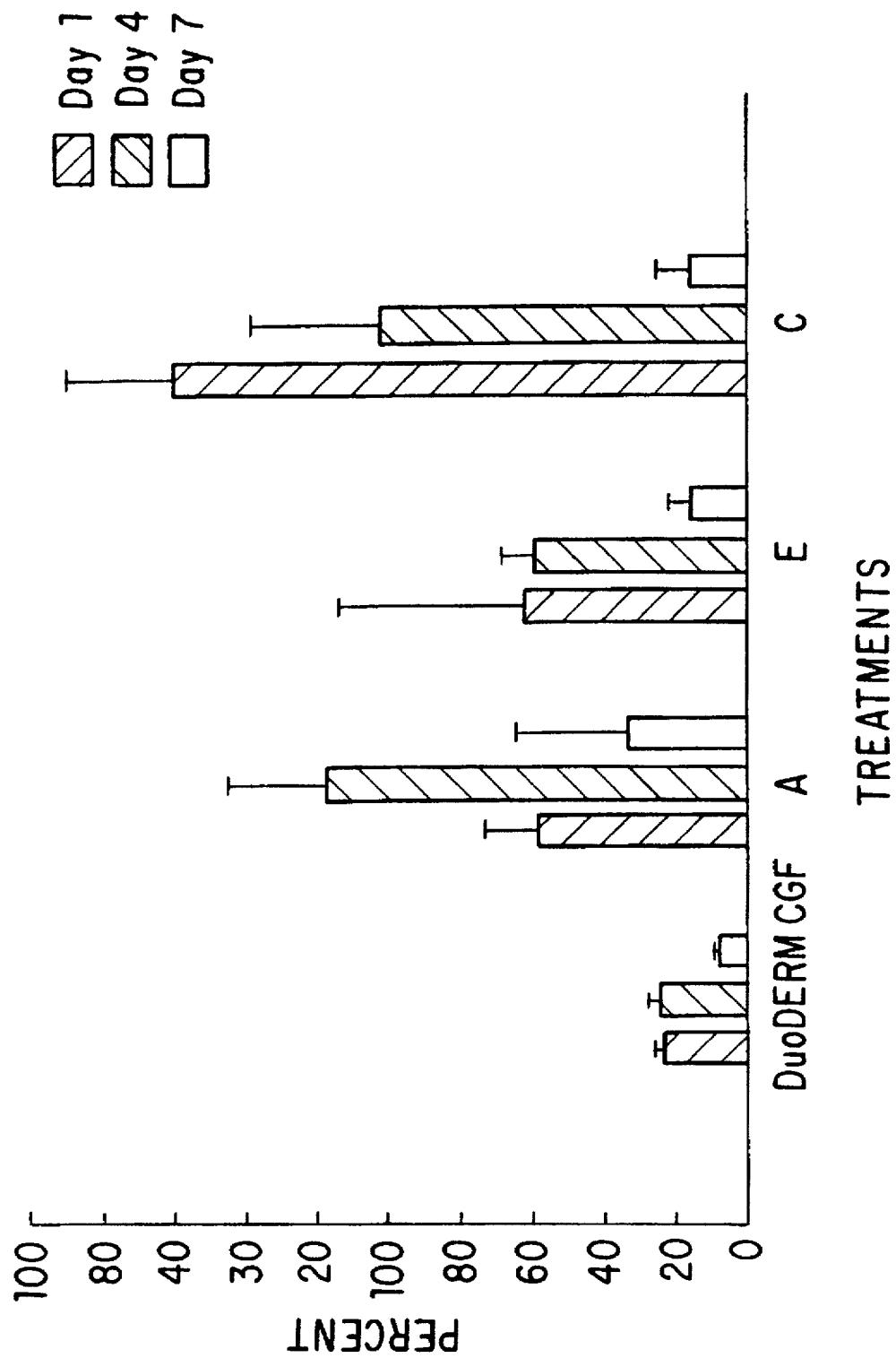
FIG. 12 is a graph showing to results of testing the dressing of the present invention showing the percent of wound fluid absorption over time.

In another preferred embodiment of the dressing of FIG. 8, the dressing comprises an occlusive layer 43 of a polyurethane film; an absorbent region 44 made up of:

a) a polymeric (e.g., Delnet) web b) a first layer of polypropylene fibers c) a mixture of hydrocolloids and superabsorbents sandwiched between the first layer of polypropylene fibers and d) a second layer of polypropylene fibers;

a polymeric support layer 45 and a thin (1–2 mil) hydrocolloid containing adhesive layer 46. The edges of this combination 47 and 48 can be heat sealed on its perimeter as shown in FIG. 9 and/or in an area adjacent to its edges 50 and 51 as shown in FIG. 11, to restrict outward flow of wound fluid. The edge sealing creates a thin cross section and minimizes the edge lifting effect found on thick hydrocolloid dressings. FIG. 10 shows the dressing of FIG. 11 in a generally circular form or with a heat seal 52 at the outer edge and another heat seal away from the edge 53.

A layer of deodorizing material can be included in the dressing if desired. Suitable deodorizing materials include a sheet of foamed polymeric material, such as polyurethane, having a large number of activated carbon particles bound to the matrix of the foam. Such a material is commercially available under the tradename K-felt (Toyobo) or Getter paper (Mead). The layer of deodorizing material will vary from about 0.010 to 0.100 inches in thickness.

In producing the dressing of the present invention the absorbent layer of the structure is prepared by conventional pad equipment. The occlusive finish and the multilayer laminate are then bonded to the absorbent layer.

The dressings and/or baseplates of the present invention represent a relatively thin, lightweight way to provide a hydrocolloid environment to a wound area and provide for rapid uptake of fluids away from the wound. Prior art dressings may include a 20–60 mil thick hydrocolloid gel adhesive layer with a foam/occlusive backing. Corresponding dressings of the present invention can utilize a 2–4 mil adhesive on a 0.5–1.5 mil polymeric support with a foam/occlusive backing and provide comparable fluid uptake and wound healing.

EXAMPLES

PRE-CLINICAL ANIMAL SCREEN

ABSTRACT: Four laboratory absorbent island prototypes consisting of various formulations, were used to evaluate wound healing in the partial thickness model. The objective was a relative comparison of prototypes A, C, E, and G with respect to absorbency, ability to retain wound fluid, and prevent leakage. Prototype C absorbed significantly more wound exudate than prototype E or the DuoDERM CGF® control dressing on post-op day 1. On day 4, prototype A absorbed more exudate than the control. Prototypes E and C were equivalent to A, and not significantly different from DuoDERM CGP®. On day 7, all prototypes absorbed equal amounts of wound fluid. Wound healing data revealed that all prototypes and the DuoDerm CGF® control showed no adverse effects to the epidermis on post-op day 4. By day 7, wounds treated with prototypes A, E, and C had a significantly slower rate of epidermal healing than wounds dressed with DuoDERM CGF®. Moisture vapor transmission rates (MVTR) passing through prototype C and E were significantly higher than A and DuoDERM CGF® on day 1. On day 4, no two groups were significantly different from each other. By day 7, only prototype C was significantly higher than all of the other prototypes and the control. On all observation days, all prototypes adequately contained wound fluid within the island layer and prevented leakage. The wound environment under the test dressings were clean and dry. A thick residue covering the surface of the wound was removed with the dressing which caused re-bleeding. There were no adverse effects observed to the surrounding skin on any treatment day.

OBJECTIVES

The purpose of this procedure is to determine:
1. The physical and mechanical problems that might occur with the use of various wound healing materials.
2. The ability to absorb wound fluids.
3. The capacity to retain absorbed wound fluids within the perimeter of the dressing.
4. The cohesiveness of the dressing.
5. The adhesive tack.

MATERIALS

DRESSING A

A solution of mineral oil gelled with polyethylene (60:40) containing 5% by weight of pectin and 5% by weight of sodium carboxymethylcellulose (NaCMC) was coated onto a perforated polypropylene film (available from Delnet). This so-formed hydrocolloid containing support layer was used to hold a 2"×2" superabsorbent containing pad (available from Gellok) centered onto a 4"×4" polyurethane foam with a polyurethane perforated film adhered to the back thereof by laminating (heat seal at edges) the polypropylene film to the foam.

DRESSING C

This was prepared as Dressing A except that the pectin and NaCMC were in a polyethylene glycol (PEG 1000) solution for coating on the polypropylene perforated film.

DRESSING E

This was prepared as Dressing A except that a double layer of the superabsorbent pad was employed.

DRESSING G

This was prepared as Dressing A except that the hydrocolloid-containing polymeric support comprised a porous polyester tissue (clean room wipe) coated with an aqueous solution of 1.5% by weight pectin, 1.5% by weight NaCMC and 2.0% by weight of polyvinylpyrrolidine.

DRESSING (Prior art)

DuoDerm CGF Hydrocolloid dressing which comprises a polyurethane occlusive backing on a polyurethane foam coated with a hydrocolloid-containing adhesive gel layer.

METHODOLOGY

Two five-way cross Yorkshire swine, weighing approximately 20 kg each, were premedicated with Ketamine® HCl 100 mg/ml, 10 mg/kg I.M prior to being clipped with standard animal clippers. The skin on both sides of the animal was prepared for wounding by washing with a soft brush and Betadine soap, followed by a warm water rinse.

The subjects were inducted with Halothane 5%, $NO_2$ @ 1.5 L/min, and $O_2$ 2.5 L/min until a surgical plane of anesthesia was reached. The animals were maintained on 1.0% Halothane, $NO_2$ and $O_2$ @ 2.5 L/min via a closed mask inhalation system.

Eight wounds measuring 22×22×0.5 mm were made in the paravertebral and thoracic regions of the animal's dorsum with a Castroviejo dermatome fitted with a 22 mm blade. The wounds were separated from one another by at least 60 mm on all sides of each wound site. Wounds were divided into treatment groups according to a randomized schedule. Dressings were changed on post-op days one and four. Evaporimeter measurements to quantify wound MVTR were conducted on post-op days four and seven. On each dressing change day, all dressings from each treatment group were photographed and assessed.

The ServoMed evaporimeter (EP1) with dual probes was used as the method of quantification. This instrument allows moisture vapor transmission to be measured under ambient conditions without forced air flow or artificially lowered relative humidity. The method is based on the estimation of the vapor pressure gradient immediately adjacent to the surface of the skin. In the case of wound healing, a low moisture vapor transmission rate indicates better wound healing.

All measurements were made at least 20 minutes after the dressing removal to allow desorption of water from the skin surface. This facilitated measurement of the true epidermal barrier function, rather than moisture retention under the dressing. Probes were held directly on the wound site for one minute or until the reading stabilized over the wound site and adjacent, non-dressed, intact skin. The moisture vapor transmission rate (MVTR) value obtained for the adjacent intact skin was subtracted from that value for the wound to yield a measure of damage to the epidermal barrier.

Statistical analysis of the evaporimeter readings can be found in Tables IA &IB. All differences reported are significant at alpha$\leq$0.05, based on a one-way analysis of variance, with the Newman-Keuls test for differences between pairs of means.

RESULTS

A. Epidermal Wound Healing (Table IA)

Analysis of the data revealed that all prototypes and the control permitted equal return of the epidermis on post-op day 4. By day 7, wounds treated with prototypes A, E, and C had a significantly slower rate of epidermal healing than wounds dressed with DuoDERM® CGF. This data was supported with visual observations of severe re-bleeding at the time of dressing removal.

Although no statistics were analyzed for prototype G (due to a small sample size, N=2), removal of the dressing caused re-injury of the wound accompanied by bleeding on post-op day 7.

B. Dressing MVTR in vivo (Table IB)

Moisture vapor transmission rates (MVTR) passing through the dressing of prototype C and E were significantly higher than A and DuoDERM CGF® on day 1. Due to the small sample size of prototype G (N=2), no statistics could be obtained comparing its MVTR values with the other prototypes. However, the mean MVTR value of prototype G was between prototypes A and E with a value of 12 g/M$^2$/hr. On day 4, no two groups were significantly higher than any of the other prototypes, including the DuoDERM CGF® control dressing.

C. Wound Fluid Absorption (Table II., FIG. 6)

On post-op day 1, prototype C absorbed significantly more wound fluid than prototype E or the DuoDERM CGF® control dressing, but was equivalent to prototype A. On day 4, only prototype A absorbed significantly more fluid than DuoDERM CGF®. Prototypes E and C were equivalent to prototype A, and not significantly different from DuoDERM CGF®. By post-op day 7, all dressings absorbed equal amounts of wound fluid.

D. SUBJECTIVE EVALUATION AND PHYSICAL PERFORMANCE

Day 0: All prototypes were easy to apply and flexible enough to conform to body contours.

Day 1: All prototypes (except for one C prototype) contained wound fluid within the island absorbent layer and prevented leakage. Prototypes C and E appeared to have more strikethrough of fluid through the foam than prototypes A, G, or the control. Removal of the prototypes revealed clean, slightly moist wound beds. Less moisture appeared under these prototypes than the amount of fluid present under the DuoDERM CGF® control. Punctuate bleeding was evident upon removal of at least one prototype from each group. It is interesting to note that while the dressings were being weighed, wounds from each group continued to secrete wound fluid.

Day 4: No leakage of wound fluid was observed from under the test dressings. Removal of the dressings revealed a clean,, dry wound environment. The peri-wound area was also dry, with no exudate residue often seen under moisture retentive dressings. Some incidence of "punctate" bleeding was documented at the time of dressing removal. The DuoDERM CGF® control dressing appeared to have condensation of fluid trapped between the film and foam which was only observed on day 4.

Day 7: Removal of the test dressings caused re-injury and in some cases severe re-bleeding. Most of the wounds were dry with a thick, dry residue covering the wound surface. Wounds dressed with prototype A appeared cleaner, without residue and little visual re-injury compared to the other treatment groups.

CONCLUSIONS

The objective of this preclinical animal study was to evaluate four prototypes with respect to absorbency, the ability to retain fluid, and prevent leakage on heavily exudating partial thickness wounds.

Although each prototype varied in formulation, each consisted of a superabsorbent layer, coated with hydrocolloid powders wrapped in Delnet and laminated onto Rossendale (DuoDERM) foam to form an absorbent island dressing. All prototypes adequately prevented leakage on all observation days.

Analysis of the data revealed that the rate of return of the epidermal barrier was equivalent for all groups on day 4. By day 7, wounds treated with the prototypes had a slower rate of healing compared to the DuoDERM CGF® control dressing. This data was supported with visual observations of disruption of the newly formed epithelium which caused re-bleeding at the time of dressing removal. The most highly exudative phase of partial thickness wounds occur within the first 4–5 days post-injury. As the wounds begin to re-epithelize, the amount of exudate decreases. Between post-op day 4 and 7, a thick residue had formed on wounds dressed with each prototype that adhered to the island layer, and this residue was removed with the dressing which caused re-bleeding.

Prototypes C and E had a significantly higher amount of moisture vapor passing through the dressing compared with the other treatment groups on day 1. Visual assessment of prototypes C and E revealed strikethrough of wound fluid through the absorbent layer and to the foam. Both prototypes had the capability of "wicking" the fluid away from the wound and peri-wound area, so much so that fluid became absorbed into the foam which resulted in a higher dressing MVTR. On day 4, all groups had equal amounts of moisture passing through the dressing. By day 7, prototype C had a significantly higher MVTR than all prototypes and the DuoDERM GCF® control dressing.

Prototype C absorbed significantly more wound fluid than prototype E or the DuoDERM CGF® control on day 1. On day 4, prototype A absorbed more fluid than the control. Prototypes E and C were equivalent to prototype A, and not significantly different from DuoDERM CGF®. On day 7, all dressings absorbed equal amounts of wound fluid.

Gross observations of the wound beds were clean and dry. Moisture retentive dressings leave a moist residue on surrounding skin. On delicate skin, this can sometimes cause irritation to the intact area. In swine, this irritation is often represented by tiny sebaceous pustulae. No irritation or adverse effects were observed to the surrounding tissue on any observation days.

TABLE 1A

Statistical Analysis of
Moisture Vapor Transmission Rate (MVTR)

A. WOUND HEALING MVTR, grams/$M^2$/hr (mean ± s.e.m.)
Wound healing evaporimetry data of two pigs with n = 3–4 wounds.
All dressings were changed on post-op days one and four.

| F value | F Prob | Day | Prototype A | Prototype C | Prototype E | DuoDERM CGF |
|---|---|---|---|---|---|---|
| .164 | .918 | 4 | 97$^a$ ± 10 n = 3 | 93$^a$ ± 2 n = 3 | 101$^a$ ± 18 n = 3 | 99$^a$ ± 3 n = 4 |
| 4.94 | .026 | 7 | 56$^a$ ± 15 n = 3 | 71$^a$ ± 5 n = 3 | 61$^a$ ± 18 n = 3 | 18$^b$ ± 3 n = 4 |

TABLE 1B

B. DRESSING MVTR, grams/$M^2$/hr (mean ± s.e.m.)

| F value | F Prob | Day | Prototype A | Prototype C | Prototype E | DuoDERM CGF |
|---|---|---|---|---|---|---|
| 10.1 | .003 | 1 | 8$^{ab}$ ± 4 n = 3 | 22$^a$ ± .6 n = 3 | 15$^{ab}$ ± 3 n = 3 | 6$^c$ ± 1 n = 4 |
| 1.04 | .420 | 4 | 18$^a$ ± .38 n = 3 | 20$^a$ ± .9 n = 3 | 17$^a$ ± 3 n = 3 | 16$^a$ ± 2 n = 4 |
| 10.09 | .002 | 7 | 5$^a$ ± 1 n = 3 | 15$^b$ ± 0 n = 3 | 5$^a$ ± 3 n = 3 | 3$^a$ ± .6 n = 4 |

COMMENTS $^{a, b, c, or d}$Means in the same row sharing the same superscript are not significantly different from each other.

TABLE II

Statistical Analysis of
Wound Fluid Absorption

Dressing weight sample size of two pigs with n = 3–4 wounds. All dressings were changed on post-op days 1 and 4.
This table represents the percent weight gain of dressings that were measured without gel or wound fluid residue.
This method departs from all past animal studies which collected exudate residue from the wound sites and weighed the material with dressings. The purpose is to assess dressing absorbency instead of total exudate.

C. PERCENT WEIGHT GAIN (mean ± s.e.m.)

| F value | F Prob | Day | Prototype A | Prototype C | Prototype E | DuoDERM CGF |
|---|---|---|---|---|---|---|
| 4.60 | .032 | 1 | 61$^{ab}$ ± 15 n = 3 | 163$^a$ ± 29 n = 3 | 64$^b$ ± 15 n = 3 | 24$^b$ ± 2 n = 4 |
| 4.37 | .036 | 4 | 119$^a$ ± 28 n = 3 | 104$^{ab}$ ± 36 n = 3 | 61$^{ab}$ ± 9 n = 3 | 25$^b$ ± 3 n = 4 |
| .587 | .638 | 7 | 35$^a$ ± 30 n = 3 | 17$^a$ ± 9 n = 3 | 17$^a$ ± 6 n = 3 | 8$^a$ ± 1 n = 4 |

COMMENTS $^{a, b, c, or d}$Means in the same row sharing the same superscript are not significantly different from each other.

I claim:

1. A skin-contacting medical device comprising a non-continuous, hydrocolloid-containing skin facing polymeric support layer allowing for the rapid uptake of wound or body fluids, an occlusive backing layer overlying said polymeric support layer, and an absorbent layer between and non-removably connected to said polymeric support layer and said occlusive layer.

2. The medical device of claim 1 wherein said medical device further comprises a skin contacting surface, said skin contacting surface having an adhesive on at least a portion thereof.

3. The medical device of claim 1 wherein said occlusive layer has a skin facing surface, said skin facing surface being larger than said polymeric support layer and wherein an adhesive is present at least on that portion of the skin-facing surface of said occlusive layer which extends beyond said polymeric support layer.

4. The medical device of claim 1 wherein said occlusive layer has a moisture vapor transmission rate of less than about 4000.

5. The medical device of claim 4 wherein said moisture vapor transmission rate is from about 100 to about 800.

6. The medical device of claim 1 wherein said occlusive layer comprises a material selected from the group consisting of a polyurethane, and a polyolefin.

7. The medical device of claim 1 wherein the occlusive layer is in a form selected from the group consisting of fibers, fibers in combination with a layer of film, a foam, and a foam in combination with a layer of film.

8. The medical device of claim 1 wherein said polymeric support layer comprises a compound selected from the group consisting of polyolefins, polyesters, polyvinyl alcohols, and polyvinyl pyrrolidone.

9. The medical device of claim 1 wherein said polymeric support layer is a water soluble polymer.

10. The medical device of claim 1 wherein the polymeric support layer further comprises at least one substance selected from the group consisting of an antibiotic, a growth factor and an accelerator.

11. The medical device of claim 2 wherein said adhesive is a pressure sensitive adhesive.

12. The medical device of claim 2 wherein said adhesive comprises an elastomeric polymeric material.

13. The medical device of claim 2 wherein said adhesive comprises a hydrocolloid.

14. The medical device of claim 1 wherein said absorbent layer comprises a fabric, foam, fiber, or web.

15. The medical device of claim 14 wherein said absorbent layer contains an absorbent selected from the group consisting of a hydrocolloid, a superabsorbent and combination thereof.

16. The medical device of claim 14 wherein said absorbent layer comprises a material selected from the group consisting of a polyolefin, a polyester and a cellulosic material.

17. The medical device of claim 14 wherein the absorbent layer comprises a superabsorbent sandwiched between plies of a web.

18. The medical device of claim 1 wherein said polymeric support layer is from about 0.5 to about 3.0 mils thick.

19. The medical device of claim 15 wherein said absorbent layer comprises said hydrocolloid and superabsorbent sandwiched between at least one polymeric layer.

20. The medical device of claim 1 in the form of a wound dressing.

21. The medical device of claim 1 in the form of an ostomy baseplate.

22. The medical device of claim 1 wherein the polymeric support layer comprises a polymeric material having a melting point of less than about 105° C.

23. The medical device of claim 1 comprising a non-continuous, hydrocolloid adhesive-containing polymeric support layer allowing for the rapid uptake of wound or body fluids; an occlusive layer of a polyurethane film; and an absorbent layer of polypropylene fibers and superabsorbents between and non-removably connected to said polymeric support layer and said occlusive layer.

24. The medical device of claim 1 comprising a performed hydrocolloid-containing film and non-continuous polymeric support layer allowing for the rapid uptake of wound or body fluids; an occlusive layer of a polyurethane film; and an absorbent layer of polypropylene fibers and superabsorbents between and non-removably connected to said polymeric support layer and said occlusive layer.

25. A wound dressing comprising:
   a) an occlusive layer of a polyurethane film;
   b) an absorbent region of:
   I) a polymeric web;
   II) a first layer of polypropylene fibers;
   III) a mixture of hydrocolloids and superabsorbents; and
   IV) a second layer of polypropylene fibers;
   c) a polymeric support layer allowing for the rapid uptake of wound or body fluids; and
   d) a hydrocolloid-containing adhesive layer.

26. The wound dressing of claim 25 comprising a heat seal along an edge of the wound dressing.

* * * * *